United States Patent
Jadhav et al.

(10) Patent No.: US 9,155,308 B2
(45) Date of Patent: Oct. 13, 2015

(54) AGRICULTURAL PESTICIDE FORMULATION

(71) Applicants: Prakash Mahadeo Jadhav, Lawrenceville, NJ (US); Stephen S. Skorczynski, Yardley, PA (US); Jaidev Rajinikant Shroff, Mumbai (IN)

(72) Inventors: Prakash Mahadeo Jadhav, Lawrenceville, NJ (US); Stephen S. Skorczynski, Yardley, PA (US); Jaidev Rajinikant Shroff, Mumbai (IN)

(73) Assignee: UPL Limited, Mumbai (IN)

( * ) Notice: Subject to any disclaimer, the term of this patent is extended or adjusted under 35 U.S.C. 154(b) by 0 days.

(21) Appl. No.: 14/212,269

(22) Filed: Mar. 14, 2014

(65) Prior Publication Data

US 2014/0274693 A1  Sep. 18, 2014

Related U.S. Application Data

(60) Provisional application No. 61/800,513, filed on Mar. 15, 2013.

(51) Int. Cl.
| | |
|---|---|
| *A01N 59/04* | (2006.01) |
| *A01N 59/06* | (2006.01) |
| *C01C 1/18* | (2006.01) |
| *C05C 7/00* | (2006.01) |
| *A01N 53/00* | (2006.01) |

(52) U.S. Cl.
CPC ...................................... *A01N 53/00* (2013.01)

(58) Field of Classification Search
None
See application file for complete search history.

(56) References Cited

U.S. PATENT DOCUMENTS

2014/0187424 A1* 7/2014 Norton et al. ................. 504/101

* cited by examiner

*Primary Examiner* — Alton Pryor
(74) *Attorney, Agent, or Firm* — VLP Law Group LLP; Kent H. Cheng

(57) ABSTRACT

The present invention provides a stable aqueous pesticide bifenthrin formulation having reduced toxicity and liquid fertilizer compatibility.

12 Claims, No Drawings

AGRICULTURAL PESTICIDE FORMULATION

CROSS-REFERENCE TO RELATED APPLICATIONS

The present application claims priority to U.S. Provisional Patent Application 61/800,513, filed Mar. 15, 2013, the entire contents of which is incorporated herein by reference.

FIELD OF THE INVENTION

The present invention relates to a stable aqueous pesticide bifenthrin formulation. In particular the present invention relates to a stable aqueous pesticide bifenthrin formulation, further comprising an anionic surfactant, a non-ionic surfactant and a rheology modifier (a hydrated aluminum-magnesium silicate). The present invention is particularly suitable in providing an insecticidal formulation having reduced toxicity and liquid fertilizer compatibility.

BACKGROUND OF THE INVENTION

Bifenthrin is a pyrethroid insecticide used against the red imported fire ant. It had a high toxicity to aquatic organisms. It is also used for the control of aphids, worms, ants, gnats, moths, beetles, grasshoppers, mites, midges, spiders, ticks, yellow jackets, maggots, thrips, caterpillars, flies, and fleas (EPA). It is often used in orchards, nurseries, and homes. It is extensively used on some crops including corn. Pesticide formulations containing bifenthrin were withdrawn from use in European Union in 2009; however, bifenthrin insecticide was reapproved for use in European Union in 2012. There have been established an acute and chronic reference dose (RfD) for bifenthrin, based on animal studies. The reference dose resembles the estimated quantity of a chemical to which a person could be exposed to every day (or a one-time exposure for the acute RfD) without any appreciable risk of adverse health effects. The acute reference dose (RfD) for bifenthrin is 0.328 mg/kg bodyweight/day. The chronic reference dose (RfD) for bifenthrin is 0.013 mg/kg bodyweight/day. Concentrations up to 10-4 M do not induce toxic effects. Commercially available bifenthrin, however, can induce toxic effects in those concentrations, because the chemicals added to the product, which for instance improve the sustainability, either potentiate bifenthrin or are themselves toxic. Symptoms of excessive exposure to bifenthrin are nausea, headaches, hypersensitivity to touch and sound and irritation of the skin and the eyes.

Bifenthrin has been formulated in variety of ways which have low concentration of bifenthrin. Most of the formulations exhibit toxicity e.g. dermal toxicity or inhalation toxicity, and contact irritation or eye irritancy, if higher concentrations of bifenthrin are used in the formulation. However, the low bifenthrin content formulations become economically unviable in agricultural applications.

Bifenthrin formulations are at times applied to the soil in fields in the form of injections. The soil applied insecticide formulation is tank mixed with a fertilizer for a combined and easier application. However when the insecticide formulation is combined with liquid fertilizer, there is a problem with reduced physical stability of the mixture due to the presence of other ingredients in the insecticide formulation like surfactants, wetting agents, viscosity modifiers and other auxiliaries, which results in degradation of the mixture leading to phase separation, creaming, flocculation, turbidity, caking, and poor performance. It is desirable that such formulations need be compatible with other formulations such as liquid fertilizers which are applied simultaneously or are mixed with the insecticide formulation prior to application.

Although various formulations of bifenthrin are available commercially, there is a need to develop a bifenthrin formulation which has reduced toxicity and good liquid fertilizer compatibility, and is environment friendly.

The present invention addresses the above mentioned drawbacks of previously known and used bifenthrin formulations.

SUMMARY OF THE INVENTION

In accordance with the present invention, the inventors of the present invention have developed a new formulation of pesticide comprising bifenthrin, an anionic surfactant, a non-ionic surfactant and a rheology modifier. The new formulation exhibits significantly lower toxicity, high stability, good fertilizer compatibility and low environmental hazard.

In yet another embodiment of the present invention, the present invention provides a method of controlling unwanted insects, the method comprising applying the composition of the present invention to the area infected by insects.

DETAILED DESCRIPTION OF THE PRESENTLY PREFERRED EMBODIMENTS

Accordingly, the present invention is directed to a stable aqueous pesticidal formulation comprising:
0.1 to 25% by weight of bifenthrin;
0.1 to 25% by weight of anionic surfactant;
0.1 to 25% by weight of non-ionic surfactant
0.1 to 25% by weight of rheology modifier Bifenthrin may be present in a concentration of from 0.1 to 25% by weight, more preferably from 10 to 20% by weight based upon the total weight of the composition.

The anionic surfactant is preferably aliphatic biodegradable taurate surfactants. Such taurate surfactants include the following commercially available taurate surfactants, such as Sodium Methyl Oleoyl taurate, Sodium Methyl Stearoyl taurate, Sodium Methyl Palmitoyl taurate, Sodium Methyl Myristoyl taurate, Sodium Methyl Lauroyl taurate, Sodium Methyl Cocoyl taurate.

Taurate surfactants contain a strongly electronegative sulfonic group and a cationic amine group. It is known that the dissociation constant of a strongly electronegative sulfonic group greatly exceeds that of cationic amine group. Thus taurates consequently demonstrate strong anionic tenedencies and minimal cationic properties.

These materials are effective in both hard & soft water, are not sensitive to lower pH, and are better wetting agents. They also show good stability to hydrolysis by acids and alkali and good dispersing power even at high temperature, and good skin compatibility.

The anionic surfactant may be present in a concentration of from 0.1 to 25% by weight, more preferably in 2 to 20% by weight based on the total weight of the composition.

The non-ionic surfactant may be selected from block polymers such as polyalkylene oxide block copolymer. More specifically, the polyalkylened oxide block copolymer is polyethylene glycol/poly(propylene)glycol block copolymer, such as Step-Flow 26 F, and polyoxoethylene polyoxopropylene-polyoxoethylene triblock copolymer, such as Pluronic P 104.

The non-ionic surfactant may be present in the concentration of from 0.1 to 25% by weight, more preferably in 0.1 to 20% by weight based on the total weight of the composition.

The rheology modifier may be a hydrated aluminum-magnesium silicate selected from montmorillonite, attapulgite, and mixtures thereof. An example of attapulgite that can be used in the composition of the present invention is Attagel. Alternatively, the rheology modifier may be sodium bentonite or a mixture of sodium bentonite and one or more hydrated aluminum-magnesium silicate.

The rheology modifier may be present in the concentration of from 0.1 to 25% by weight, more preferably from 0.5 to 20% by weight based on the total weight of the composition.

A preferable composition of the present invention comprises:
bifenthrin 0.1 to 25% by weight, more preferably 15 to 25% by weight
Geropon T-77: 3.5% to 7.5% by weight
Stepflow: 0.2% to 2.7% by weight
Attagel: 3.5% to 7.5% by weight Accordingly the formulation may further comprise an antifreeze agent such as propylene glycol. The antifreeze agent may be present in the concentration of from 0.1 to 25% by weight, more preferably from 0.5 to 20% by weight based on the total weight of the composition.

The formulation may further comprise anti foaming agents, such as silicone-based defoamers. One example is Dow Corning 1500.

The formulation may further comprise a biocide, such as 1,2-benzisothiazolin-3-one (Proxel GXL).

The composition may further comprise an insecticidally effective amount of one or more additional insecticides selected from the group consisting of imidacloprid, thiamethoxam, flonicamid, thiacloprid, nitenpyram, clothianidin, and fipronil.

In the preferred process of making the preferable composition discussed above, all the ingredients except the Attagel are premixed with water to produce an homogeneous slurry. This slurry is then milled to a preferred particle size. When miffing is complete, the Attagel is added to obtain a preferred viscosity.

The above composition of the present invention may be diluted with a liquid fertilizer to produce an insecticidal fertilizer composition comprising an insecticidal composition comprising
a. bifenthrin;
b. a hydrated aluminum-magnesium silicate;
c. an anionic aliphatic biodegradable taurate surfactant; and
d. non-ionic polyalkylene oxide block copolymer surfactant; and a liquid fertilizer. The liquid fertilizer may be present in a concentration of from 95.0% by weight to 99.99% by weight based upon the total weight of all components of the insecticidal fertilizer composition. This insecticidal fertilizer composition would then be applied to the soil.

Alternatively, the above composition of the present invention may be diluted with water and applied to the soil without prior mixing with a liquid fertilizer.

Whether the composition is mixed with a liquid fertilizer or water, it is preferable that the amount of bifenthrin provides for an effective amount bifenthrin insecticide (Active Ingredient) on spraying 40 to 50 Gallons of the total mixture per Acre.

In yet another embodiment of the present invention, the present invention provides a method of controlling unwanted insects, the method comprising applying the composition of the present invention to the area infected by insects. The present invention provides a method of controlling insects and providing nutrition to the plant comprising combining the composition of the present invention with a liquid fertilizer and applying the mixture to the area infested with insects.

The compositions of the present invention exhibit low toxicity. The lower toxicity of the composition of the present invention results in less skin irritation and sensitization to the user, less eye irritation, lesser inhalation toxicity and lower contact toxicity. The compositions of the present invention have high storage stability. When mixed with the liquid fertilizer, the resultant mixture did not show any degradation, indicating compatibility of the two.

Examples

The compositions of the present invention are further illustrated by the examples below. The examples are only to illustrate the invention and should not be interpreted as limiting the scope of the invention since further modifications of the disclosed invention may be apparent to those skilled in the art. All such modifications are deemed to be within the scope of the claimed invention.

Shown below are the results of the toxicity studies conducted on the composition of the present invention. The toxicity studies were conducted based on US EPA Health Effects Test Guidelines OPPTS 870.1200 and complying with Good Laboratory Practices (GLP), as well as regulations defined in 40 CFR 160: US EPA GLP standards.

The composition that was tested for toxicity contains the following ingredients:

| | |
|---|---|
| Bifenthrin | 17.5% -Stepflow 26 F   0.6% - polyalkylene oxide block copolymer |
| Geropon T-77 | 5.2% sodium 2[methyloleoylamino] ethane-1-sulphonate (also known as sodium - N-methyl oleyl taurate) |
| Propylene Glycol | 8.3% - 1,2-propanediol |
| Attagel 40 | 5.0% - attapulgite clay |
| Dow Corning 1500 | 0.5% silicone compound |
| Proxel GXL | 0.2% aqueous solution of 1,2-benzisothiazolin-3-one |
| Water | 62.7% |
| Total | 100.00% |

Toxicity Results:

Table comparing the final results from our GLP acute toxicity testing of KFD 110-03, an embodiment of the present invention, with those published in the Capture LFR MSDS.

| Test | Result Capture* | Tox Cat | Result KFD 110-03** | Tox Cat |
|---|---|---|---|---|
| Acute Oral | 175 mg/kg | II | 550 mg/kg | III |
| Acute Dermal | >5,000 mg/kg | IV | >5,000 mg/kg | IV |
| Acute Inhalation | >2.28 mg/L | IV | >5.08 mg/L | IV |
| Eye Irritation | Mildly Irritating | III | Mildly Irritating | III |
| Skin Irritation | Slightly irritating | IV | Non-irritating | IV |
| Dermal Sensitization | Non-sensitizing | N/A | Non-sensitizing | N/A |
| Signal word | | Warning | | Caution |

*Market sample with 17.5% bifenthrin content
**formulation of the present invention The above toxicity results indicate that the above formulation of the present invention will likely be certified by the Environmental Protection Agency as less toxic than the bifenthrin-containing insecticidal composition presently marketed as Capture.

The following are the test methods used to determine product stability, water dispersion stability and stability upon mixing with a liquid fertilizer (NPK stability). Stability testing upon mixing with liquid fertilizer was conducted with varying amounts of nitrogen, phosphorus ($P_2O_5$) and potassium ($K_2O$). More specifically, the N/P/K relative amounts in the liquid fertilizer that were tested are 11-37-0 and 7-21-5. Further, we expect that the insecticidal composition of the present invention is compatible with a liquid fertilizer having N/P/K relative amounts as follows:

i. 19-19-19
ii. 15-15-15
iii. 10-10-10
iv. 6-12-12
v. 12-24-24
vi 5-10-15
vii. 18-46-0
viii. 11-37-0

Product stability (Physical state) after storage under accelerated conditions at 54 C for 14 days was determined under MT 46.3 Accelerated Storage Procedure published by CIPAC and prepared by the German Formulation Panel.

The following tables A-1, A-2 and A-3 show the stability on water dilution and fertilizer compatibility results when the amount of Geropon T-77 is varied while keeping the amount of all other ingredients constant:

TABLE A

Compositions with Different Concentrations of Geropon T-77

| | Batch # | | | | | | | |
|---|---|---|---|---|---|---|---|---|
| | #508-47A | #508-47B | #508-47C | #508-47D | #508-47E | #508-47F | #508-47G | #508-47H |
| Bifenthrin Technical | 17.5 | 17.5 | 17.5 | 17.5 | 17.5 | 17.5 | 17.5 | 17.5 |
| Geropon T-77 | 10.0 | 8.0 | 7.5 | 6.5 | 5.8 | 5.2 | 4.0 | 3.0 |
| Stepflow 26F | 0.6 | 0.6 | 0.6 | 0.6 | 0.6 | 0.6 | 0.6 | 0.6 |
| Propylene Glycol | 8.3 | 8.3 | 8.3 | 8.3 | 8.3 | 8.3 | 8.3 | 8.3 |
| Dow Corning 1500 | 0.5 | 0.5 | 0.5 | 0.5 | 0.5 | 0.5 | 0.5 | 0.5 |
| Proxel GXL | 0.2 | 0.2 | 0.2 | 0.2 | 0.2 | 0.2 | 0.2 | 0.2 |
| Attagel 40 | 5.0 | 5.0 | 5.0 | 5.0 | 5.0 | 5.0 | 5.0 | 5.0 |
| Water | 57.9 | 59.9 | 60.4 | 61.4 | 62.1 | 62.7 | 63.9 | 64.9 |

TABLE A-1

Results of Dispersion Stability Test on Dilution in Water Procedure in CIPAC MT 180

| | Criteria | Batch # | | | | | | | |
|---|---|---|---|---|---|---|---|---|---|
| | | #508-47A | #508-47B | #508-47C | #508-47D | #508-47E | #508-47F | #508-47G | #508-47H |
| Initial observation (presence of sediment, cream, or oil) | Negligible | Negligible | Negligible | Negligible | Negligible | Negligible | Negligible | Negligible | Negligible |
| Sediment volume after 2 hrs | 0.1 mL max. | <0.05 | 0.10 | 0.10 | 0.10 | 0.10 | <0.05 | <0.05 | 0.15 |
| Top layer of cream or oil volume after 4 hrs | <0.1 mL | <0.1 | <0.1 | <0.1 | <0.1 | <0.1 | <0.1 | <0.1 | <0.1 |
| Result | Pass/Fail | Pass | Pass | Pass | Pass | Pass | Pass | Pass | Fail |

Inference: #508-47H failed on the independent criteria of sediment volume after 2 hours. All other batches passed.

TABLE A-2

Results of Dispersion Stability Test on Dilution in Liquid Fertilizer Procedure in CIPAC MT 180

| | Criteria | Batch # | | | | | | | |
|---|---|---|---|---|---|---|---|---|---|
| | | #508-47A | #508-47B | #508-47C | #508-47D | #508-47E | #508-47F | #508-47G | #508-47H |
| Initial observation (presence of sediment, cream, or oil) | Negligible | Negligible | Negligible | Negligible | Negligible | Negligible | Negligible | Negligible | Negligible |
| Sediment volume after 4 hrs | 0.1 mL max. | <0.1 | <0.1 | <0.1 | <0.1 | <0.1 | <0.1 | <0.1 | <0.1 |
| Top cream or oil volume after 8 hrs | <1.0 mL | <1.0 | <1.0 | <1.0 | 1.0 | <1.0 | <1.0 | <1.0 | 1.0 |
| Result | Pass/Fail | Pass | Pass | Pass | Pass | Pass | Pass | Pass | Pass |

Inference: All batches passed the dispersion stability test on dilution in liquid fertilizer.

TABLE A-3

Results of Physical Degradation after Accelerated Conditions Aging Test Procedure: CIPAC MT 46.3, testing in 100 mL glass bottle for 14 days at 54 C.

| | | Batch # | | | | | | | |
|---|---|---|---|---|---|---|---|---|---|
| | Criteria | #508-47A | #508-47B | #508-47C | #508-47D | #508-47E | #508-47F | #508-47G | #508-47H |
| pH (1% solution) | 7.0-9.0 | 8.3 | 8.5 | 8.5 | 8.5 | 8.4 | 8.4 | 8.4 | 8.6 |
| Viscosity, spindle 63 at 20 C. | 200-400 cps | 500 | 400 | 350 | 324 | 300 | 332 | 260 | 240 |
| Layer separation | 2.0% max | 4.5% | 3.5% | 1.0% | 1.0% | 1.0% | 1.0% | 1.0% | 1.0% |
| Sedimentation | 1.0% max | 2.5% | 1.5% | 0.5% | 0.5% | <0.5% | <0.5% | <0.5% | 0.5% |
| Result | Pass/Fail | Fail | Fail | Pass | Pass | Pass | Pass | Pass | Pass |

Inference: #508-47A failed on the independent criteria of viscosity, layer separation, and sedimentation and #508-47B failed on the independent criteria of layer separation and sedimentation. All other batches passed.

Conclusions:
1). Batch #508-47A, #508-47B, #508-47H fail.
2). Batch #508-47C, #508-47D, #508-47E, #508-47F, #508-47G pass.

The following tables B-1, B-2 and B-3 show the stability on water dilution and fertilizer compatibility results when the amount of Stepflow 26F is varied while keeping the amount of all other ingredients constant:

TABLE B

Compositions with Different Concentrations of Stepflow 26F

| | Batch # | | | | | | | |
|---|---|---|---|---|---|---|---|---|
| | #508-47I | #508-47J | #508-47K | #508-47L | #508-47M | #508-47N | #508-47O | #508-47P |
| Bifenthrin Technical | 17.5 | 17.5 | 17.5 | 17.5 | 17.5 | 17.5 | 17.5 | 17.5 |
| Geropon T-77 | 5.2 | 5.2 | 5.2 | 5.2 | 5.2 | 5.2 | 5.2 | 5.2 |
| Stepflow 26F | 3.0 | 2.7 | 2.4 | 2.0 | 1.0 | 0.6 | 0.2 | 0.0 |
| Propylene Glycol | 8.3 | 8.3 | 8.3 | 8.3 | 8.3 | 8.3 | 8.3 | 8.3 |
| Dow Corning 1500 | 0.5 | 0.5 | 0.5 | 0.5 | 0.5 | 0.5 | 0.5 | 0.5 |
| Proxel GXL | 0.2 | 0.2 | 0.2 | 0.2 | 0.2 | 0.2 | 0.2 | 0.2 |
| Attagel 40 | 5.0 | 5.0 | 5.0 | 5.0 | 5.0 | 5.0 | 5.0 | 5.0 |
| Water | 60.3 | 60.6 | 60.9 | 61.3 | 62.3 | 62.7 | 63.1 | 63.3 |

TABLE B-1

Results of Dispersion Stability Test on Dilution in Water Procedure in CIPAC MT 180

| | Criteria | #508-47I | #508-47J | #508-47K | #508-47L | #508-47M | #508-47N | #508-47O | #508-47P |
|---|---|---|---|---|---|---|---|---|---|
| Initial observation (presence of sediment, cream, or oil) | Negligible | Negligible | Negligible | Negligible | Negligible | Negligible | Negligible | Negligible | Negligible |
| Sediment volume after 2 hrs | 0.1 mL max. | 0.5 | <0.05 | <0.05 | <0.05 | <0.05 | <0.05 | <0.05 | <0.05 |
| Top layer of cream or oil volume after 4 hrs | <0.1 mL | <0.1 | <0.1 | <0.1 | <0.1 | <0.1 | <0.1 | <0.1 | <0.1 |
| Result | Pass/Fail | Fail | Pass | Pass | Pass | Pass | Pass | Pass | Pass |

Inference: #508-47I failed on the independent criteria of sediment volume after 2 hours. All other batches passed.

TABLE B-2

Results of Dispersion Stability Test on
Dilution in Liquid Fertilizer
Procedure in CIPAC MT 180

| | Criteria | Batch # | | | | | | | |
|---|---|---|---|---|---|---|---|---|---|
| | | #508-47I | #508-47J | #508-47K | #508-47L | #508-47M | #508-47N | #508-47O | #508-47P |
| Initial observation (presence of sediment, cream, or oil) | Negligible | Negligible | Negligible | Negligible | Negligible | Negligible | Negligible | Negligible | Negligible |
| Sediment volume after 4 hrs | 0.1 mL max. | <0.1 | <0.1 | <0.1 | <0.1 | <0.1 | <0.1 | <0.1 | <0.1 |
| Top cream or oil volume after 8 hrs | <1.0 mL | <1.0 | <1.0 | <1.0 | <1.0 | <1.0 | <1.0 | <1.0 | <1.0 |
| Result | Pass/Fail | Pass | Pass | Pass | Pass | Pass | Pass | Pass | Pass |

Inference: All batches passed the dispersion stability test on dilution in liquid fertilizer.

TABLE B-3

Results of Physical Degredation after
Accelerated Conditions Aging Test
Procedure: CIPAC MT 46.3, testing in 100 mL glass
bottle for 14 days at 54 C.

| | Criteria | Batch # | | | | | | | |
|---|---|---|---|---|---|---|---|---|---|
| | | #508-47I | #508-47J | #508-47K | #508-47L | #508-47M | #508-47N | #508-47O | #508-47P |
| pH (1% solution) | 7.0-9.0 | 8..3 | 8.3 | 8.4 | 8.4 | 8.6 | 8.5 | 8.3 | 8.5 |
| Viscosity, spindle 63 at 20 C. | 200-400 cps | 350 | 300 | 275 | 250 | 216 | 210 | 200 | 132 |
| Layer separation | 2.0% max | <2.0% | <2.0% | <2.0% | <2.0% | <2.0% | <2.0% | <2.0% | <2.0% |
| Sedimentation | 1.0% max | <1.0% | <1.0% | <1.0% | <1.0% | <1.0% | <1.0% | <1.0% | <1.0% |
| Result | Pass/Fail | Pass | Pass | Pass | Pass | Pass | Pass | Pass | Fail |

Inference: #508-47P failed on the independent criteria of viscosity. All other batches passed
Conclusions:
1). Batch #508-47I, #508-47P fail.
2). Batch #508-47J, #508-47K, #508-47L, #508-47M, #508-47N, #508-47O pass.

The following tables C-1, C-2 and C-3 show the stability on water dilution and fertilizer compatibility results when the amount of Attagel 40 is varied while keeping the amount of all other ingredients constant:

TABLE C

Compositions with different concentrations of hydrated aluminum magnesium silicate (Attagel 40)

| | Batch # | | | | | | |
|---|---|---|---|---|---|---|---|
| | #508-47O | #508-47P | #508-47Q | #508-47R | #508-47S | #508-47T | #508-47U |
| Bifenthrin Technical | 17.5 | 17.5 | 17.5 | 17.5 | 17.5 | 17.5 | 17.5 |
| Geropon T-77 | 5.2 | 5.2 | 5.2 | 5.2 | 5.2 | 5.2 | 5.2 |
| Stepflow 26F | 0.6 | 0.6 | 0.6 | 0.6 | 0.6 | 0.6 | 0.6 |

TABLE C-continued

Compositions with different concentrations of hydrated aluminum magnesium silicate (Attagel 40)

| | Batch # | | | | | | |
|---|---|---|---|---|---|---|---|
| | #508-47O | #508-47P | #508-47Q | #508-47R | #508-47S | #508-47T | #508-47U |
| Propylene Glycol | 8.3 | 8.3 | 8.3 | 8.3 | 8.3 | 8.3 | 8.3 |
| Dow Corning 1500 | 0.5 | 0.5 | 0.5 | 0.5 | 0.5 | 0.5 | 0.5 |
| Proxel GXL | 0.2 | 0.2 | 0.2 | 0.2 | 0.2 | 0.2 | 0.2 |
| Attagel 40 | 11.0 | 9.5 | 8.0 | 5.5 | 4.5 | 3.0 | 1.0 |
| Water | 56.7 | 58.2 | 59.7 | 62.2 | 63.2 | 64.7 | 66.7 |

TABLE C-1

Results of Dispersion Stability Test on
Dilution in Water
Procedure in CIPAC MT 180
applicable to suspension
concentrate

| | | Batch # | | | | | | |
|---|---|---|---|---|---|---|---|---|
| | Criteria | #508-47O | #508-47P | #508-47Q | #508-47R | #508-47S | #508-47T | #508-47U |
| Initial observation (presence of sediment, cream, or oil) | Negligible | Negligible | Negligible | Negligible | Negligible | Negligible | Negligible | Negligible |
| Sediment volume after 2 hrs | 0.1 mL max. | <0.1 | <0.1 | <0.1 | <0.1 | <0.1 | <0.1 | <0.1 |
| Top layer of cream or oil volume after 4 hrs | <0.1 mL | <0.1 | <0.1 | <0.1 | <0.1 | <0.1 | <0.1 | <0.1 |
| Result | Pass/Fail | Pass | Pass | Pass | Pass | Pass | Pass | Pass |

Conclusion: All batches passed the dispersion stability test on dilution in water.

TABLE C-2

Results of Dispersion Stability Test on
Dilution in Liquid Fertilizer
Procedure in CIPAC
MT 180

| | | Batch # | | | | | | |
|---|---|---|---|---|---|---|---|---|
| | Criteria | #508-47O | #508-47P | #508-47Q | #508-47R | #508-47S | #508-47T | #508-47U |
| Initial observation (presence of sediment, cream, or oil) | Negligible | Negligible | Negligible | Negligible | Negligible | Negligible | Negligible | Negligible |
| Sediment volume after 4 hrs | 0.1 mL max. | <0.1 | <0.1 | <0.1 | <0.1 | <0.1 | <0.1 | <0.1 |
| Top cream or oil volume after 8 hrs | <1.0 mL | 1.5 | 1.5 | 1.0 | <1.0 | <1.0 | <1.0 | 1.5 |
| Result | Pass/Fail | Fail | Fail | Pass | Pass | Pass | Pass | Fail |

Conclusion: #508-47O, #508-47P and #508-47U failed on the independent criteria of creaming in liquid fertilizer. All other batches passed.

TABLE C-3

Results of Physical Degredation after
Accelerated Conditions Aging Test
Procedure: CIPAC MT 46.3, testing in 100 mL glass
bottle for 14 days at 54 C.

| | | Batch # | | | | | | |
|---|---|---|---|---|---|---|---|---|
| | Criteria | #508-47O | #508-47P | #508-47Q | #508-47R | #508-47S | #508-47T | #508-47U |
| pH (1% solution) | 7.0-9.0 | 8.6 | 8.3 | 8.2 | 8.4 | 8.4 | 8.3 | 8.5 |
| Viscosity, spindle 63 at 20 C. | 200-400 cps | 550 | 500 | 425 | 304 | 200 | 175 | 150 |
| Layer separation | 2.0% max | <2.0% | <2.0% | <2.0% | <2.0% | <2.0% | <2.0% | <2.0% |
| Sedimentation | 1.0% max | <1.0% | <1.0% | <1.0% | <1.0% | <1.0% | <1.0% | <1.0% |
| Result | Pass/Fail | Fail | Fail | Fail | Pass | Pass | Fail | Fail |

Conclusion: #508-47O through #508-47Q and #508-47T and #508-47U failed on the independent criteria of viscosity. All other batches passed.

The invention is not limited by the embodiments described above which are presented as examples only but can be modified in various ways within the scope of protection defined by the appended patent claims.

We claim:

1. An insecticidal composition comprising
   a) 0.1 to 25% by weight of bifenthrin;
   b) 0.1 to 25% by weight of a hydrated aluminum-magnesium silicate;
   c) 0.1 to 25% by weight of an anionic aliphatic biodegradable taurate surfactant;
   d) 0.1 to 25% by weight of non-ionic polyalkylene oxide block copolymer surfactant; and
   e) 0.1 to 25% by weight of an antifreeze agent.

2. The insecticidal composition of claim 1 wherein the non-ionic block copolymer surfactant is selected from the group consisting of polyethylene glycol/poly(propylene)glycol block copolymer and polyoxoethylene polyoxopropylene-polyoxoethylene triblock copolymer.

3. The insecticidal composition of claim 1 wherein the hydrated aluminum-magnesium silicate is selected from the group consisting of montmorillonite, attapulgite, and mixtures thereof.

4. The insecticidal composition of claim 1 wherein the hydrated aluminum-magnesium silicate is attapulgite.

5. The insecticidal composition of claim 1 wherein the anionic aliphatic biodegradable taurate anionic surfactant is selected from the group consisting of Sodium Methyl Oleoyl taurate, Sodium Methyl Stearoyl taurate, Sodium Methyl Palmitoyl taurate, Sodium Methyl myristoyl taurate, Sodium Methyl lauroyl taurate, and Sodium Methyl cocoyl taurate.

6. The insecticidal composition of claim 1 wherein the anionic aliphatic biodegradable taurate surfactant is sodium 2[methyloleoylamino]ethane-1-sulphonate.

7. The insecticidal composition of claim 1, further comprising at least one of an anti-foam agent and a biocide.

8. The insecticidal composition of claim 1, comprising 15 to 25% by weight of bifenthrin.

9. The insecticidal composition of claim 1, comprising:
   15 to 25% by weight of bifenthrin;
   3.5% to 7.5% by weight of sodium 2[methyloleoylamino]ethane-1-sulphonate;
   0.2% to 2.7% by weight of polyethylene glycol/poly(propylene)glycol block copolymer; and
   3.5% to 7.5% by weight of attapulgite.

10. The insecticidal composition of claim 1, comprising:
    17.5% by weight of bifenthrin;
    5.2% by weight of sodium 2[methyloleoylamino]ethane-1-sulphonate;
    0.6% by weight of polyethylene glycol/poly(propylene)glycol block copolymer; and
    5.0% by weight of attapulgite.

11. The insecticidal composition of claim 1 further comprising sodium betonite.

12. An insecticidal fertilizer composition comprising an insecticidal composition comprising
    a. 0.1 to 25% by weight of bifenthrin;
    b. 0.1 to 25% by weight of a hydrated aluminum-magnesium silicate;
    c. 0.1 to 25% by weight of an anionic aliphatic biodegradable taurate surfactant;
    d. 0.1 to 25% by weight of non-ionic polyalkylene oxide block copolymer surfactant;
    e) 0.1 to 25% by weight of an antifreeze agent;
    and a liquid fertilizer.

* * * * *